(12) United States Patent
Kats et al.

(10) Patent No.: US 9,557,315 B2
(45) Date of Patent: Jan. 31, 2017

(54) CONFINING PRESSURE MEASUREMENT FOR ZONAL ISOLATION EVALUATION

(71) Applicant: SCHLUMBERGER TECHNOLOGY CORPORATION, Sugar Land, TX (US)

(72) Inventors: Roman Kats, Brookline, MA (US); Agathe Robisson, Cambridge, MA (US); Simone Musso, Cambridge, MA (US); Yucun Lou, Belmont, MA (US); Jeffrey Thomas, Winchester, MA (US)

(73) Assignee: SCHLUMBERGER TECHNOLOGY CORPORATION, Sugar Land, TX (US)

( * ) Notice: Subject to any disclaimer, the term of this patent is extended or adjusted under 35 U.S.C. 154(b) by 642 days.

(21) Appl. No.: 13/953,196

(22) Filed: Jul. 29, 2013

(65) Prior Publication Data

US 2015/0027217 A1    Jan. 29, 2015

(51) Int. Cl.
 *G01N 33/38* (2006.01)
(52) U.S. Cl.
 CPC .................................. *G01N 33/383* (2013.01)
(58) Field of Classification Search
 CPC ....................................................... G01N 33/383
 See application file for complete search history.

(56) References Cited

U.S. PATENT DOCUMENTS

| | | | | |
|---|---|---|---|---|
| 4,359,901 A | * | 11/1982 | Bates | E21B 49/005 73/152.11 |
| 5,159,828 A | * | 11/1992 | Steiger | E21B 49/006 73/38 |
| 5,226,310 A | * | 7/1993 | Steiger | E21B 49/006 73/38 |
| 5,243,855 A | * | 9/1993 | Stieger | E21B 49/006 73/152.52 |
| 5,253,518 A | * | 10/1993 | Steiger | E21B 49/006 166/250.01 |
| 5,265,461 A | * | 11/1993 | Steiger | G01N 29/07 73/38 |
| 5,275,063 A | * | 1/1994 | Steiger | G01N 33/241 73/865.6 |
| 5,359,903 A | * | 11/1994 | Steiger | G01N 29/07 73/862.627 |
| 5,589,650 A | * | 12/1996 | Flemming | B22C 19/04 164/456 |
| 5,747,674 A | * | 5/1998 | Moracchini | G01N 25/00 73/152.18 |

(Continued)

FOREIGN PATENT DOCUMENTS

WO    2011051675 A2    5/2011

OTHER PUBLICATIONS

"Report of the Presidential Commission on the Space Shuttle Challenger Accident", Feb. 3, 1986, 54 pages.

(Continued)

*Primary Examiner* — John Fitzgerald
(74) *Attorney, Agent, or Firm* — Bridget M. Laffey; Jakub Michna

(57) ABSTRACT

Apparatus and methods for measuring confining pressure, axial strain and radial strain of zonal isolation materials are described. This information is useful for evaluating these materials and predicting seal performance and potential failures of these materials.

24 Claims, 12 Drawing Sheets

(56) References Cited

U.S. PATENT DOCUMENTS

| | | | | |
|---|---|---|---|---|
| 6,817,238 | B2* | 11/2004 | Go Boncan | G01N 33/383 73/149 |
| 7,189,575 | B2* | 3/2007 | Schrof | G01N 19/10 356/27 |
| 7,240,545 | B1* | 7/2007 | Jennings | G01F 22/00 73/149 |
| 8,434,355 | B1* | 5/2013 | Bi | G01N 15/088 73/152.05 |
| 8,443,661 | B1* | 5/2013 | Bi | G01N 33/24 73/152.05 |
| 8,794,078 | B2* | 8/2014 | Darbe | G01N 3/10 73/803 |
| 2008/0168848 | A1* | 7/2008 | Funkhouser | G01N 3/10 73/865.6 |
| 2013/0228019 | A1* | 9/2013 | Meadows | G01N 3/08 73/821 |
| 2013/0340505 | A1* | 12/2013 | Go Boncan | G01N 33/383 73/38 |
| 2014/0007695 | A1* | 1/2014 | Darbe | G01N 3/10 73/803 |

OTHER PUBLICATIONS

Achenbach, M., "Service life of seals—numerical simulation in sealing technology enhances prognoses", Computational Materials Science, vol. 19, 2000, pp. 213-222.

Baltrus, et al., "Screening of Potential O-Ring Swelling Additives for Ultraclean Transportation Fuels", Ultraclean Transportation Fuels, Chapter 15, ACS Symposium Series, vol. 959, 2007, pp. 197-208.

Bhavsar, et al., "Intelligence in Novel Materials", Oilfield Review, 2008, pp. 32-41.

Boesch, Donald, "Deep-water drilling remains a risky business", Nature, vol. 484, Apr. 19, 2012, p. 289.

Cai, et al., "Force generated by a swelling elastomer subject to constraint", Journal of Applied Physics, vol. 107, 2010, 7 pages.

Flory, et al., "Statistical Mechanics of Cross—Linked Polymer Networks—I. Rubberlike Elasticity", Journal of Chemical Physics, vol. 11, 1943, pp. 512-520.

Flory, et al., "Statistical Mechanics of Cross—Linked Polymer Networks—II. Swelling", Journal of Chemical Physics, vol. 11, 1943, pp. 521-526.

Hembling, et al., "Aramco uses swell packers to enable smart open-hole, multilateral completions for EOR", Drilling Contractor, Sep./Oct. 2007, pp. 108-114.

Horst, et al., "Compression stress relaxation apparatus for the long-time monitoring of the incremental modulus", Review of Scientific Instruments, vol. 74 (11), Nov. 2003, pp. 4737-4744.

Katti, et al., "Influence of swelling on the microstructure of expansive clays", Canadian Geotechnical Journal, vol. 38 (1), 2001, pp. 175-182.

Kim, et al., "Approximation of contact stress for a compressed and laterally one side restrained O-ring", Engineering Failure Analysis, vol. 14 (8), Dec. 2007, pp. 1680-1692.

Lou, et al., "Swellable elastomers under constraint", Journal of Applied Physics, vol. 112, 2012, 7 pages.

* cited by examiner

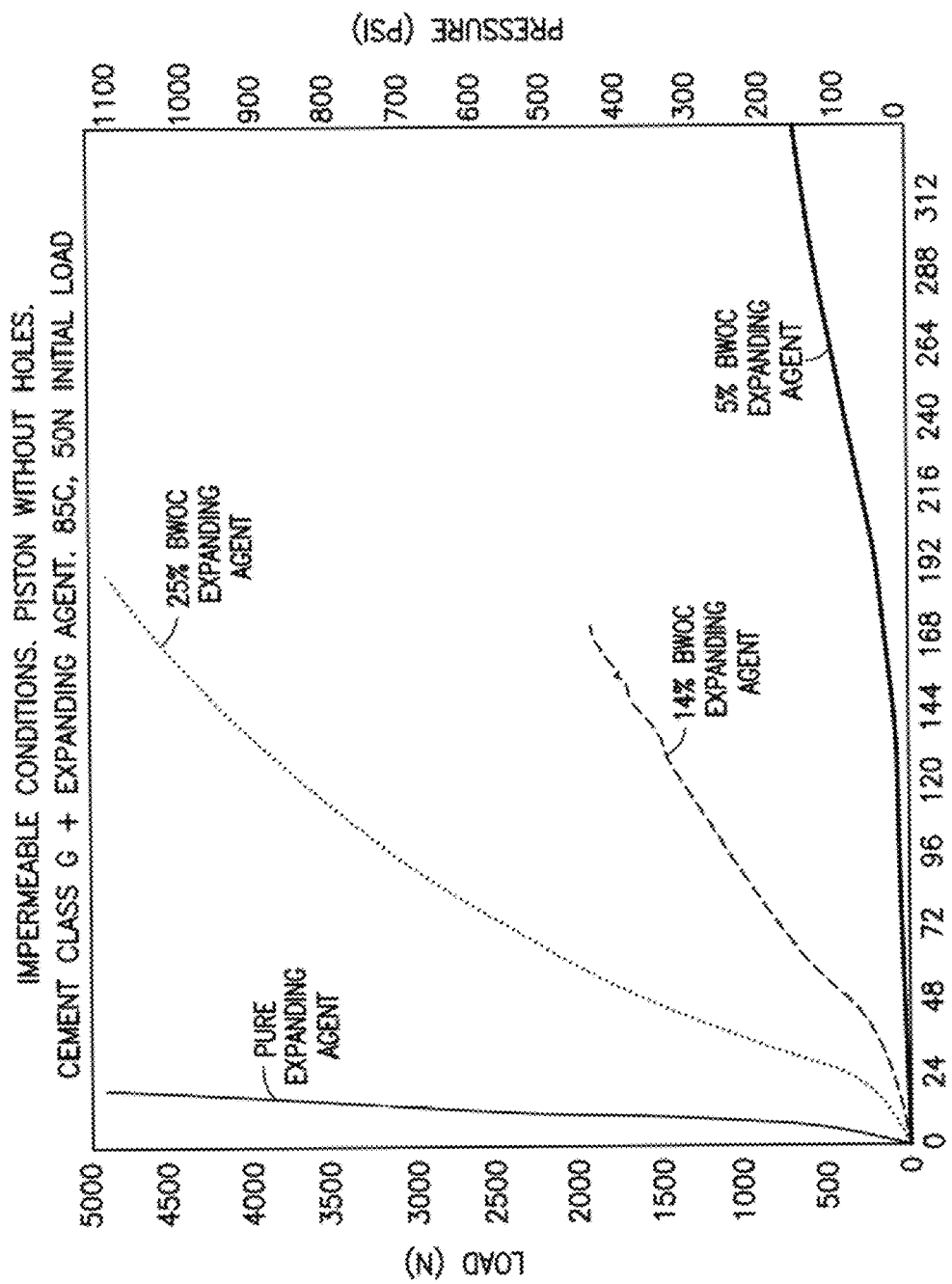

CONFINING PRESSURE MEASUREMENT FOR ZONAL ISOLATION EVALUATION

FIELD

The subject disclosure generally relates to materials used for zonal isolation. More particularly, the subject disclosure relates to apparatus and methods for evaluating these materials.

BACKGROUND

Zonal isolation, defined as sealing of the wellbore against unwanted movement of fluids, is a significant challenge for safely extracting oil and gas from offshore and deepwater reservoirs, and has become one of the most important environmental concerns for the oilfield industry (Boesch, D. "Deepwater drilling remains a risky business". Nature 484: 289, 2012). In the worst-case scenario, oil or gas moves vertically upward from the reservoir along the borehole and escapes into the surrounding land or seabed. In particular, zonal isolation is a significant challenge for producing shale gas reservoirs due to the stresses generated in the wellbore by hydraulic fracturing, which can damage the isolation material.

The standard approach to zonal isolation is to pump cement slurry into the annular space between the formation and production casing and allow it to harden in place. Ensuring long-term zonal isolation requires a durable material with low permeability and reasonably high compressive strength that completely fills the annular space. Another approach to sealing, widely used in the automotive and aerospace industries and increasingly used in the oilfield, is to utilize gaskets, O-rings and packers made of elastomers. For these applications, the seal provides a localized block against fluid flow. The maximum differential pressure that the seal can sustain is primarily determined by the contact pressure between the seal material and its confinement, and by the modulus of the seal material (Kim et al, "Approximation of contact stress for a compressed and laterally one side restrained O-ring. Eng Fail Anal 14: 1680-92, 2007). In some cases, the seal relies on its swelling. The ability to seal is crucial to the functioning of diverse components (from a refrigerator or a car to a space shuttle) and sealing failures are responsible for a significant fraction of mechanical breakdowns, leading sometimes to catastrophic results.

Once a zonal isolation material, example, cement or rubber is placed in an annular gap between the formation and a casing/liner hanger or tubing and the casing, the material is expected to exert a load against the confinement (either the formation or the casing/liner hanger). If no compressive load is present, any movement of the confining medium (casing undergoing positive hoop strain for example) or the base tube (tubing undergoing negative hoop strain for example), may cause the sealing to be lost. This type of movement happens regularly in oil wells where the temperature and pressure fluctuate due to pumping and producing cycles. It is important therefore to be able to predict seal performance and potential failure of materials which are used in zonal isolation.

SUMMARY

This summary is provided to introduce a selection of concepts that are further described below in the detailed description. This summary is not intended to identify key or essential features of the claimed subject matter, nor is it intended to be used as an aid in limiting the scope of the claimed subject matter.

In an embodiment, an apparatus is disclosed for measuring a swelling pressure and swelling kinetics of a sample. The apparatus comprises: an external container; an internal container disposed inside the external container; a base member coupling the external and internal container, the base member comprising a heating element; a sample inside the internal container wherein the sample swells on contact with a swelling agent; a piston operative to slide axially inside the internal container; and a mechanical testing device connected to the piston to determine at least one of a force and a displacement exerted by the sample on the piston as the sample swells, wherein the internal container confines the sample in a radial direction and the piston position controls a sample length.

In an embodiment, a method for evaluating a sample (if material used for zonal isolation is disclosed. The method comprises: disposing an internal container inside an external container; placing a sample of material inside the internal container, wherein the material swells on contact with a swelling agent; coupling the external and internal container with a base member comprising a heating module; placing a piston above the sample of material, the piston operative to slide axially inside the internal container; and using a mechanical testing device in contact with the piston and determining at least one of force and displacement exerted by the sample of material on the piston as the sample of material swells.

Further features and advantages of the subject disclosure will become more readily apparent from the following detailed description when taken in conjunction with the accompanying drawings.

BRIEF DESCRIPTION OF THE DRAWINGS

The subject disclosure is further described in the detailed description which follows, in reference to the noted plurality of drawings by way of non-limiting examples of the subject disclosure, in which like reference numerals represent similar parts throughout the several views of the drawings, and wherein:

FIGS. 10A and 10B are graphs of the confinement load (FIG. 10A) and corresponding pre-stress (FIG. 10B) developed in expanding cement slurries;

DETAILED DESCRIPTION

Figure 1:
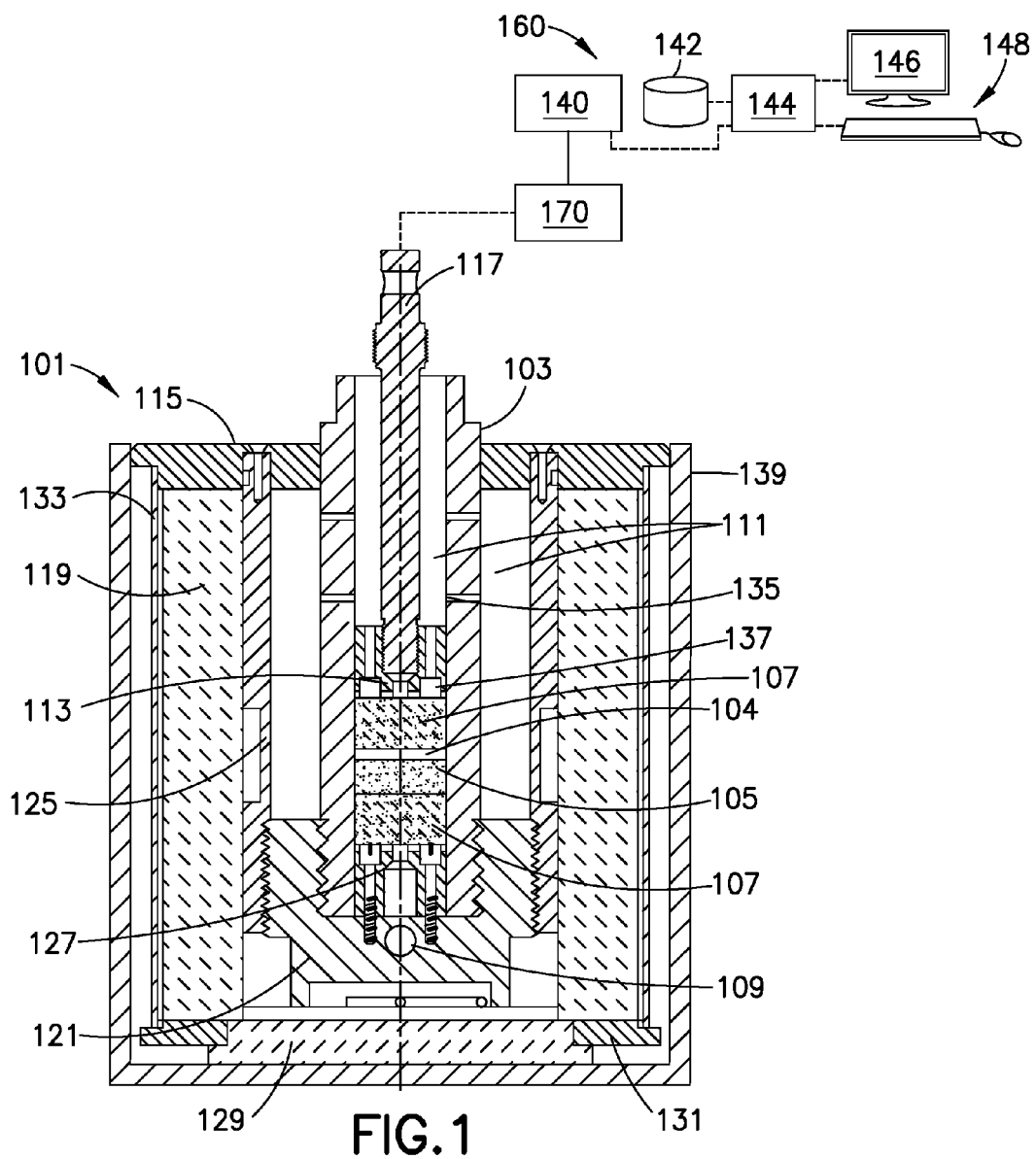
FIG. 1 depicts an embodiment of the subject disclosure used for determining swelling pressure.

The particulars shown herein are by way of example and for purposes of illustrative discussion of the examples of the subject disclosure only and are presented in the cause of providing what is believed to be the most useful and readily understood description of the principles and conceptual aspects of the subject disclosure. In this regard, no attempt is made to show structural details in more detail than is necessary, the description taken with the drawings making apparent to those skilled in the art how the several forms of the subject disclosure may be embodied in practice. Furthermore, like reference numbers and designations in the various drawings indicate like elements.

Predicting seal performance and potential failure are complex tasks. The subject disclosure provides an apparatus and method which can help predict the ability of a material to seal by accurately measuring the contact pressure that is developed under downhole conditions which includes temperature, confinement, and the fluid environment.

In general, when a swellable component swells under confinement, it absorbs less solvent, than under non-confinement. As a result, providing the material is still in contact with and has access to the solvent, the gel system (polymer and solvent mixture) applies a pressure against the confinement. This pressure is often called swelling pressure and is equivalent to osmotic pressure. This swelling pressure is important to initiate the sealing in for example, a swellable packer. After the sealing is initiated, the material is submitted to a differential pressure and the equilibrium sealing ability depends not only on the swelling pressure but also on the mechanical properties of the swollen rubber.

In embodiments, a sample of a material to be tested is placed inside a confinement container, in non-limiting examples to cylinder. The sample may be in a solid form (e.g. rubber disks), or in liquid form (e.g. freshly mixed cement slurry) and the geometry of the sample may vary depending on the container which is used, for example, a cylindrical sample of material is used when the confinement container is cylindrical. Above and below the sample may be placed porous ceramic disks filled with fluid that is accessible to the sample and may diffuse into the sample. In some embodiments, the fluid diffusion is in the axial direction only and no solvent can permeate in the radial direction. The swelled sample is constrained in the radial direction by the internal cylinder and is constrained in the axial direction by the top and bottom ceramic disks. As the material swells, the force on the piston is recorded as a function of time, which is easily converted to the contact stress, by dividing the force by the cross-sectional area of the sample. Below the bottom ceramic disk, a steel lower support is screwed into the confinement cylinder. Above the upper ceramic disk, and in direct contact, is a piston that slides axially inside the steel cylinder. The shaft of the piston is connected to a load cell that records the load over time. The gap between the sample and the ceramic disk can be adjusted which will impact the swelling/expanding ratio. In an embodiment, one or both porous disks may be removed, in a non-limiting example, to simulate contact with a tight or dry formation. In non-limiting examples, the device is heated with a heating jacket coupled to the internal and external cylinder or in other situations the device may be heated using for example an oven. A control thermocouple is placed in the fluid, while a backup security thermocouple is placed in the heating jacket.

In an embodiment, devices heat the sample at a temperature below the boiling point of the fluid so that no pressure compensation is needed. Direct access to the fluid is available from above and below as the confining cylinder has openings that allow the fluid to enter from the surrounding bath to the inside of the cylinder, above and below the sample and ceramic disks.

In an embodiment, the device may be modified to enable testing above the fluid boiling point. A pressure cell may be designed to hold the fluid and the sample and a dynamic seal may be used around the shaft to transition from a high pressure to atmospheric pressure. In other embodiments, the entire apparatus is placed inside a pressurized chamber (139) and the air in the chamber is pressurized so that as high pressure is reached and the water will not boil at that pressure.

FIG. 1 is a schematic drawing of an apparatus (101) of the subject disclosure. FIG. 1 depicts a confinement device or inner cylinder (103) which is used to restrict radial swelling. The inner cylinder (103) is contained within an external cylinder (125) and the external cylinder (125) comprises a fluid. This fluid may be water, oil or any other fluid known to those skilled in the art may be used. The liquid is able to enter the inner cylinder (103) through openings (135) and through piston openings (137) which allow for fluid transfer and circulation.

In this setup, a cylindrical sample (105) is placed in the hollow metallic internal cylinder (103) of same diameter. In one example, the internal diameter of the metallic tube is about 29 mm and the external diameter is about 50 mm. As shown, the apparatus (101) is configured to measure swelling of an elastomeric material in contact with swelling fluid (111). In non-limiting examples, this swelling fluid may be oil, brine, water, etc. Surrounding the inner (103) and outer cylinder (125) is a brass base (121) which comprises a heater (109).

The outer layer of the apparatus comprises a fiberglass heat resistant insulating material (119) which is surrounded on the outside by a soft carbon steel outer skin (133). The top of the apparatus comprises a lid (115) made from a PEEK material. The bottom of the apparatus comprises a bottom supporting plate (131), and a ceramic insulating plate (129). Similar to the lid (115) the bottom supporting plate (131) comprises a PEEK material. Above and below the sample (105) are placed porous ceramic disks (107). In a non-limiting example, these ceramic disks consisting of aluminum oxide with connected porosity and an average pore size of about 90 microns, which guarantees that the permeation of the solvent through the plate is much faster than the permeation of the solvent through the sample. The liquid diffusion is 2-dimensional, as no solvent can permeate in the radial direction. At the bottom of the porous ceramic disk (107) is a lower support (127) and in non-limiting examples, this lower support (127) has openings which may be opened or closed and allow fluid circulation in the cylinder. The upper piston and lower supports (113 and 127) may comprise stainless steel. Along the axial direction, lower support (127) is fixed, and the upper piston (113) is in contact with a shaft (117) connected to a processing facility (160) which includes a load cell. The ceramic disks are made of a porous material. In a non-limiting example, the porosity is about 50%. These disks are stiff compared to the sample so that we can neglect their deformation. These disks also have the ability to absorb a lot of liquid which is then available for absorption by the sample (105). Above the top ceramic disk is the piston (113) head. The gap (104) between the sample (105) and the ceramic disk (107) can be adjusted, and this adjustment controls the swelling ratio. The solvent liquid can flow inside the cylinder above and below the ceramic disks (107). The whole setup is heated with a heating jacket which comprises a heating element (109). A control thermocouple is placed in the liquid and a security check thermocouple is placed in the heating jacket. The shaft is finally connected to a mechanical testing device (170) and the load is recorded. The mechanical testing device (170) is part of a processing facility (160) which includes one or more central processing units (140), storage system (142), communications and input/output modules (144), a user display (146) and a user input system (148). Input/output modules (144) include modules to communicate with and control the mechanical testing device (170).

The apparatus may also be used in a force control mode: the processing facility (160) allows axial movement of the shaft (117) to follow the swelling at zero force for example, or at any other force, corresponding to a swelling pressure.

The processing facility (160) may include a multipurpose mechanical testing device (170) that would record both the force and displacement as a function of time that is generated by the sealing material under confinement. Non-limiting examples of multipurpose mechanical testing devices (170) include INSTRON® testing machine, Mark-10® or a simple manual test machine. These results are used to quantify the kinetics of elastomer-swelling or cement-hydration under confined downhole conditions. In non-limiting examples, these multipurpose mechanical testing devices (170) are able to measure both a displacement which corresponds to the axial strain of a sample being tested and a load which corresponds to the confinement pressure of the sample being tested. In the configuration shown, in FIG. 1, the gap (104) requires the sample material (105) to first swell to a certain amount before generating any confinement. The porous ceramic disks (107) provide a fluid environment to simulate the formation, which in this case is oil.

Figure 2:
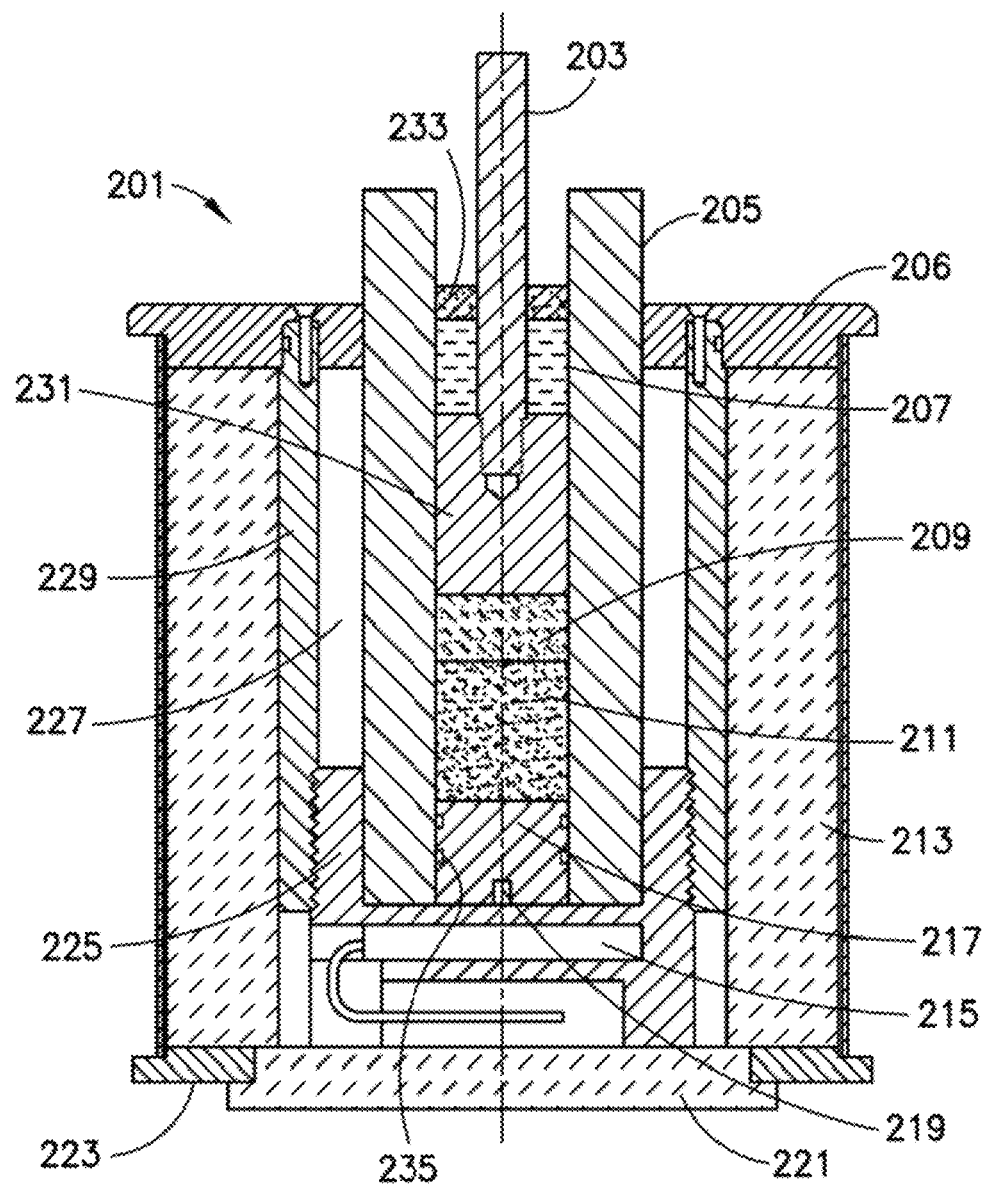
FIG. 2 depicts an embodiment of the subject disclosure used for determining swelling pressure.

FIG. 2 depicts an apparatus (201) for measuring swelling pressure. The apparatus is configured to measure the prestress development of cement slurry in contact with a water-filled formation. The piston (231) may be connected to a multipurpose mechanical testing device, similar to the multipurpose mechanical testing device (170) of FIG. 1 that records the development of confining pressure with time.

Similar to the previous apparatus (101), a steel confinement cylinder (205) contains the cement sample (211). A porous ceramic disk (209) is in contact with the top of the cement sample (211). At the bottom of the cement sample is a lower support (217) and a plurality of o-rings (235) to seal the cylinder. In some embodiments, the lower support (217) comprises a slot (219). This slot (219) allows for easier removal of the samples once the experiments are completed. The steel confinement cylinder (205) is surrounded by an external cylinder (229) which contains a heat transmissive liquid (227). In this instance, the liquid is used for heating the apparatus so that the temperature is consistent throughout the apparatus and is not absorbed by the cement sample. In this configuration, the fluid is not transferred via openings to the inner cylinder (205) and the purpose of this liquid is to heat the apparatus and maintain the sample (211) at a steady temperature.

In non-limiting examples, a filter paper may be used which is in direct contact with the ceramic disks. The filter paper prevents the cement slurry from contaminating or clogging the ceramic disks. The upper porous ceramic disk (209) is in contact with an upper support plate (231). A shaft (203) is connected below to the piston (231) head and above to a multipurpose mechanical resting machine (170 of FIG. 1). In embodiments, external curing liquid (207) is located above the upper support plate (231) and provides for an additional reservoir of fluid which is available to the sample (211). A layer of high boiling-point silicon oil (233) may be added to prevent evaporation of the fluid (207). A thin layer of high temperature lubricant may be painted on the outer surface of the piston (231), the lower support plate (217), and the inner surface of the confinement cylinder (205). The lubricant prevents adhesion of the cement material (211) to the metal surfaces, reducing friction of the piston (231) and preventing metal oxidation.

Surrounding the inner (205) and outer cylinder (229) is a brass base (225) which comprises a heater (215). The outer layer of the apparatus comprises a heat resistant insulating material (213) which is surrounded on the outside by an outside skin. The top of the apparatus comprises a lid (206) and the bottom of the apparatus comprises a bottom supporting plate (223) and a ceramic insulating plate (221).

Figure 3A:
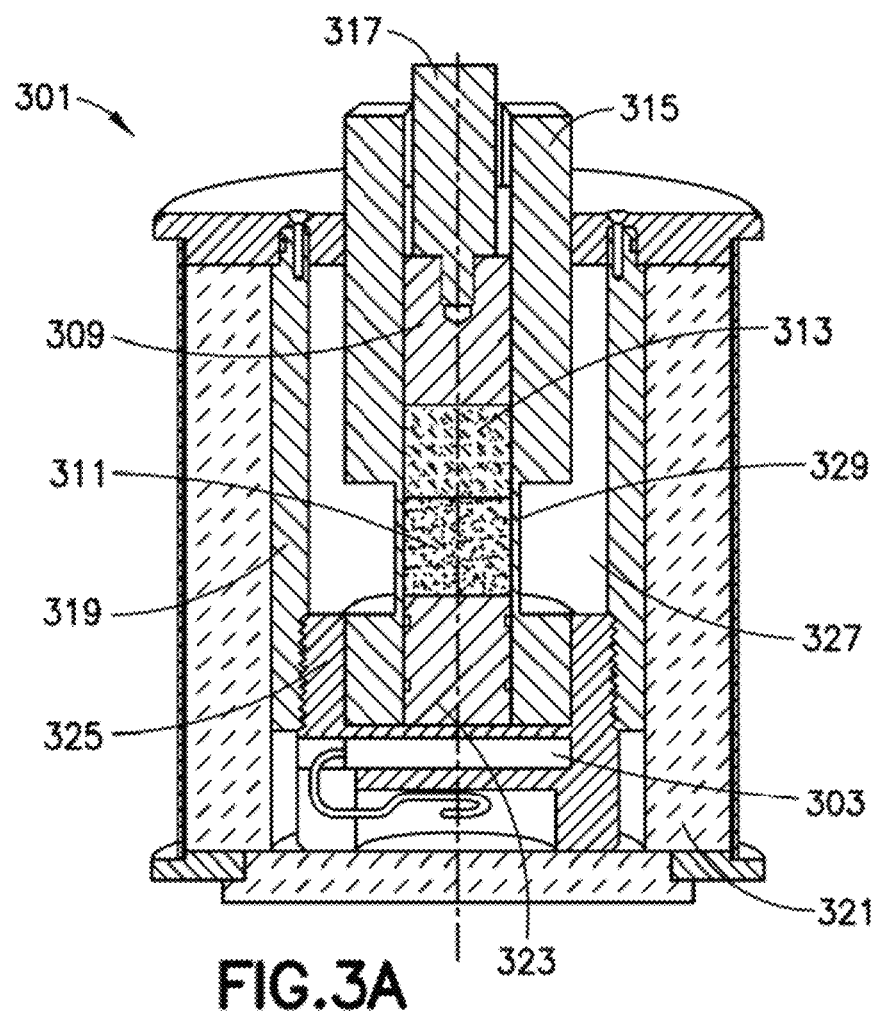
FIGS. 3A and 3B depicts an embodiment of the subject disclosure used for determining swelling pressure, the apparatus configured to measure axial and radial swelling of a material.
Figure 3B:
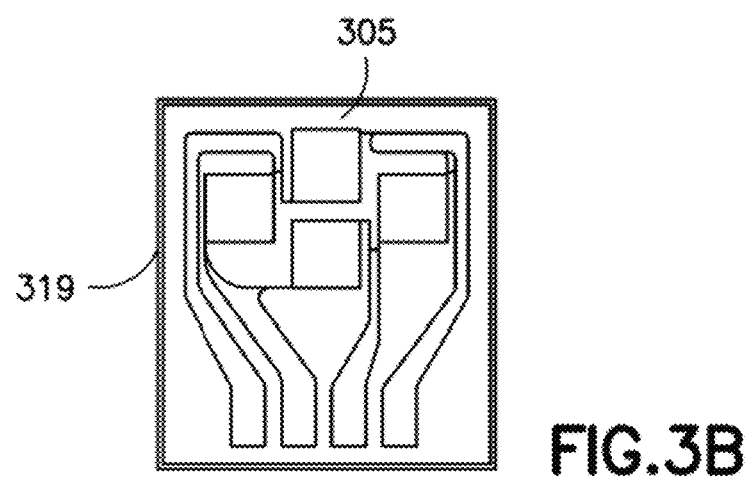

FIGS. 3A and 3B depict an apparatus (301) for measuring swelling pressure. The apparatus (301) is configured to measure both axial and radial swelling of a material, in a non-limiting example cement (311). In a laboratory setting, the piston (309) may be connected to a multipurpose mechanical testing device that records the development of confining pressure with time. In some embodiments, a porous ceramic disk (313) containing curing liquid may be added between the piston (309) and the cement (311), the porous ceramic disk (313) providing a fluid environment to simulate the formation.

A portion of the internal cylinder (315) comprises a thin wall (329) which is used to measure radial strain with a strain gauge (305). FIG. 3B depicts a strain gauge (305) which can be placed on the external surface of the metal internal cylinder (315) using in a non-limiting example an adhesive. The thin wall (329) elastically deforms and this deformation is measured by the strain gauge (305). In a non-limiting example, the strain gauge is placed near the middle of the sample (311), in other examples; the strain gauge (305) is placed between the top and the bottom of the sample. Silicone sealant may be used to prevent fluid contact on the strain gauge (305).

Similar to the previous embodiments, an upper porous ceramic disk (313) is in contact with an upper support plate (309). A rod (317) is connected below to the piston (309) head and above to a multipurpose mechanical testing device (170 in FIG. 1). At the bottom of the cement sample (311) is a lower support (323) and a plurality of o-rings to seal the internal cylinder (315).

Surrounding the inner (315) and outer cylinder (319) is a brass base (325) which comprises a heating element (303). The outer layer of the apparatus comprises a heat resistant insulating material (321) which is surrounded on the outside by an outside skin. The top of the apparatus comprises a lid and the bottom of the apparatus comprises a bottom supporting plate and a ceramic insulating plate. Heat transmissive liquid (327) is situated between the outer cylinder (319) and the inner cylinder (315) which is used to regulate the temperature of the device.

Figure 4:
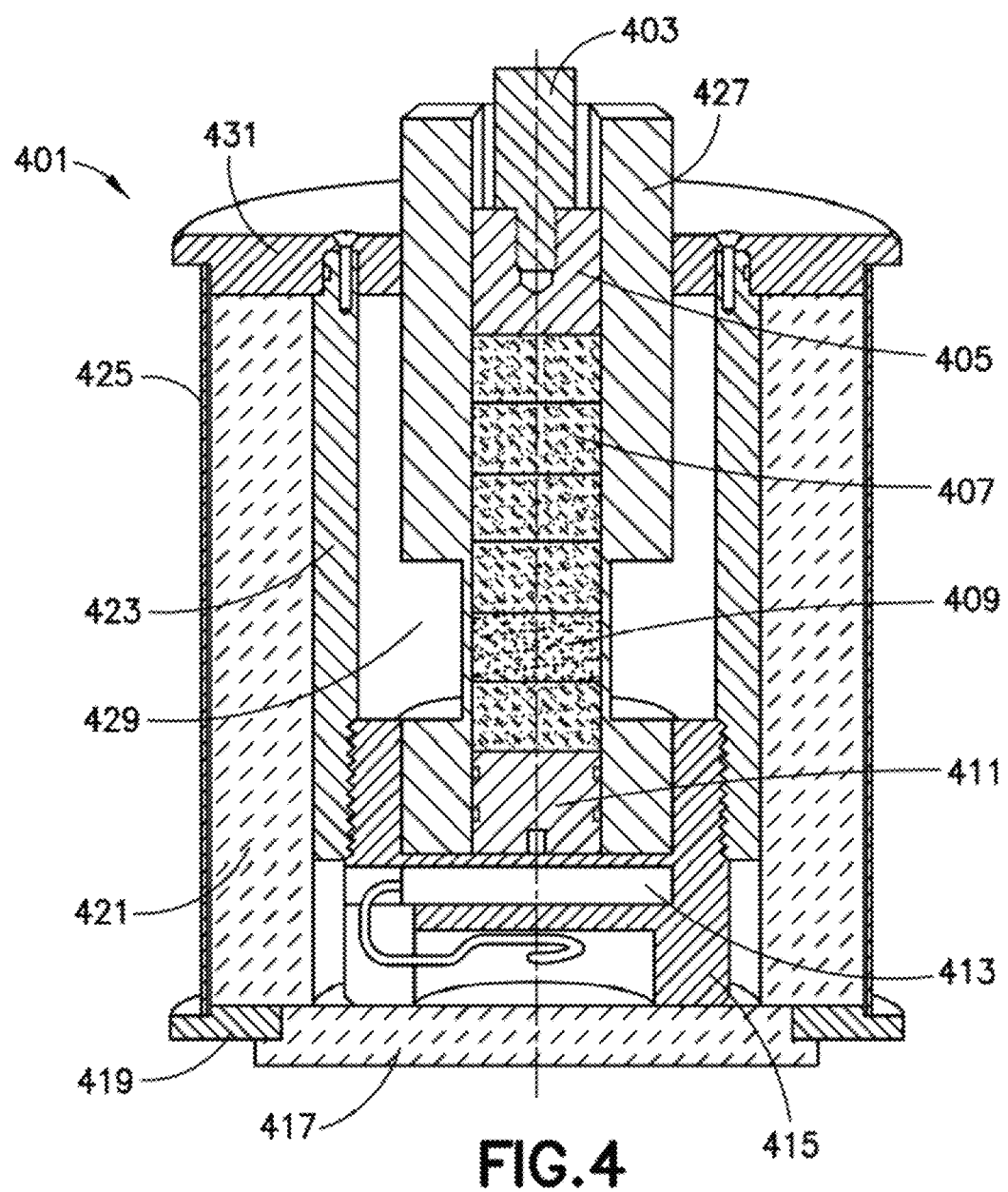
FIG. 4 depicts an embodiment of the subject disclosure used for determining swelling pressure.

FIG. 4 depicts an apparatus (401) for measuring swelling pressure. The apparatus (401) comprises a plurality of porous ceramic disks (407) one on top of the other. An advantage of the plurality of porous ceramic disks (407) is the availability of curing, liquid for the sample (409) especially in cases where the volume of the sample is increased.

This is especially important for cement slurries. In these situations, the plurality of ceramic disks (407) provides uniform hydration to the sample (409).

Similar to the previous embodiments, the uppermost porous ceramic disk (407) is in contact with an upper support plate (405). A rod (403) is connected below to the piston (405) head and above to a multipurpose mechanical testing device (not shown). At the bottom of the lowermost porous ceramic disk (407) are a lower support (411) and a plurality of o-rings which are used to seal the internal cylinder (427).

Surrounding the inner cylinder (427) and the outer cylinder (423) is a brass base (415) which comprises a heating element (413). The outer layer of the apparatus comprises a heat resistant insulating material (421) which is surrounded on the outside by an outside skin. The top of the apparatus comprises a lid (431) and the bottom of the apparatus comprises a bottom supporting plate (419) and a ceramic insulating plate (417). Heat transmissive liquid (429) is situated between the outer cylinder (423) and the inner cylinder (427) which is used to regulate the temperature of the device.

Figure 5B:
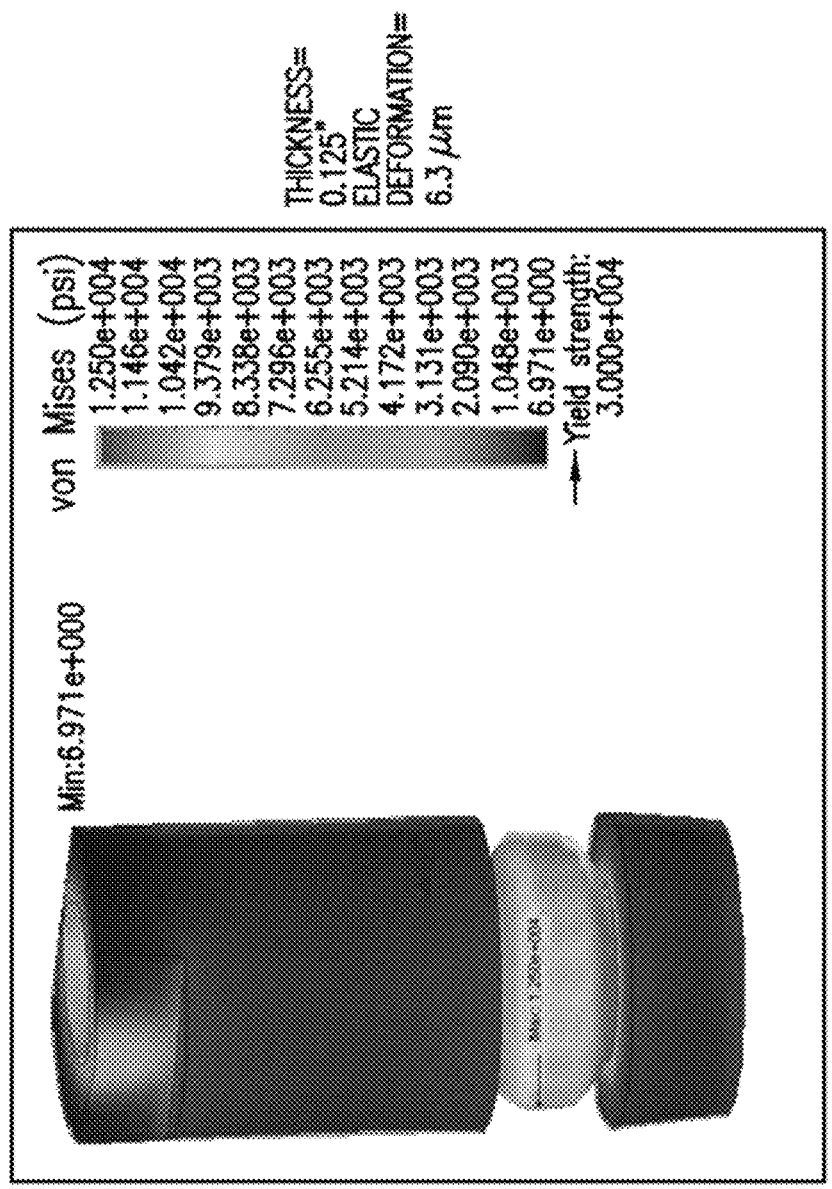
FIGS. 5A-5C depicts a finite element analysis of the elastic deformation of a thin wall of a cylinder under a maximum pressure of 1136.8 psi (confine load of 5000N)
Figure 5A:
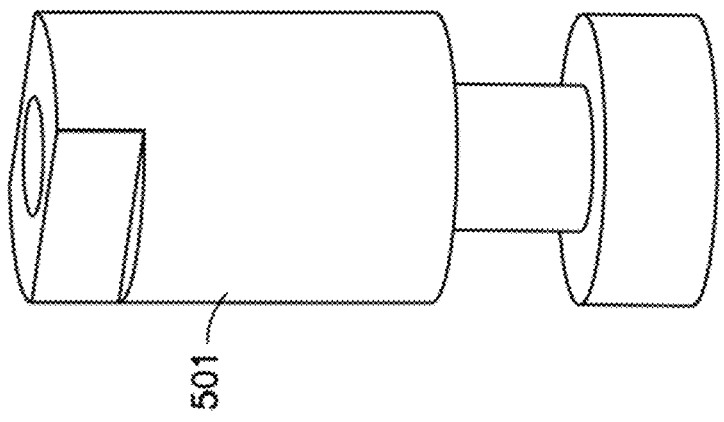
Figure 5C:
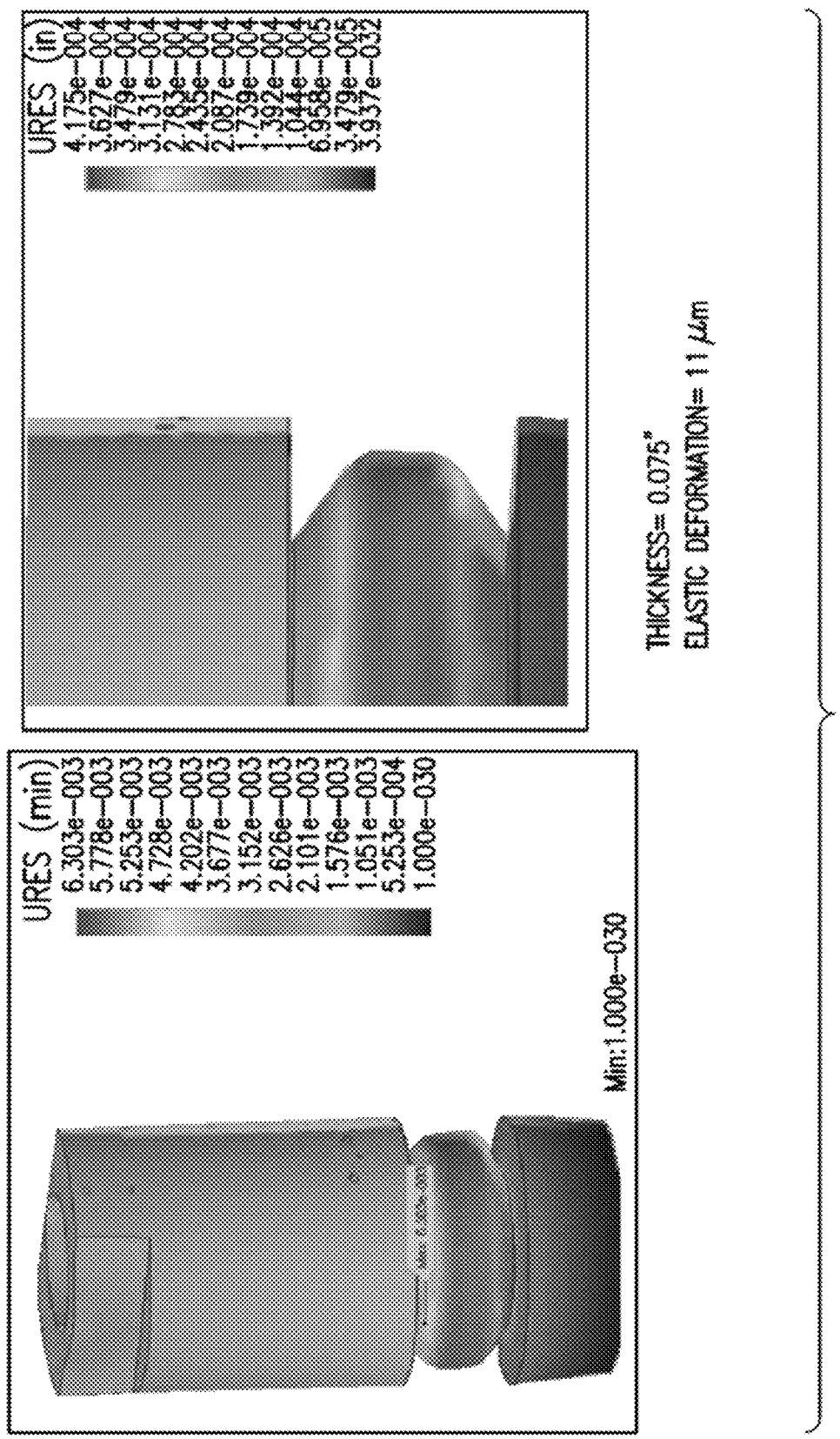

FIGS. 5A-5C depicts a finite element analysis of the elastic deformation of a thin wall of a confining cylinder, similar to the thin wall (319) above, under a maximum pressure of 1136.8 psi (confine load is 5000 N). The inner diameter of the cylinder (501) is about 1.25" as shown in FIG. 5A. The finite element analysis is a computational model, to predict what happens with the thin wall of the cylinder under pressure. If the wall is very thin then it will not be able to withstand the pressure resulting in plastic deformation or breakage. Different thicknesses were simulated and the elastic deformation was calculated. FIG. 5B shows a cylinder with a thickness of 0.125" and elastic deformation of 6.3 µm and FIG. 5C shows a cylinder with a thickness of 0.075" and elastic deformation of 11 µm.

Figure 6:
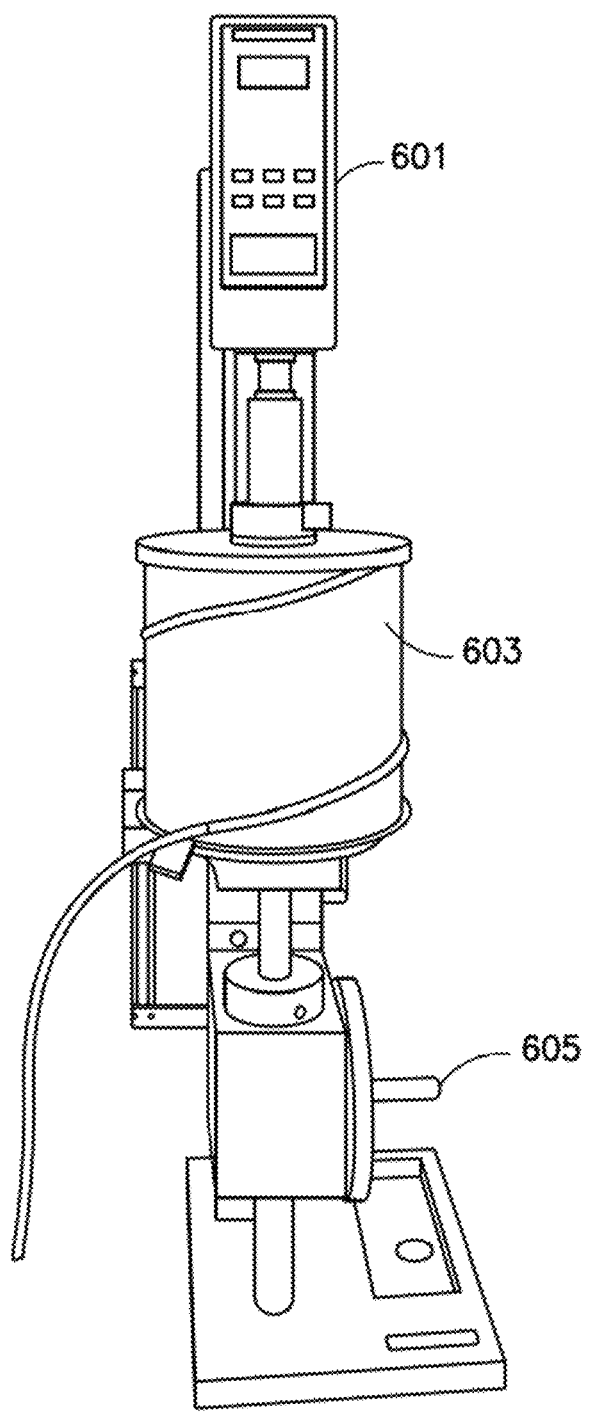
FIG. 6 depicts a drawing of a confinement pressure device of an embodiment of the subject disclosure.

FIG. 6 depicts a confinement pressure device of an embodiment of the subject disclosure. The device is mounted on a portable test stand. The device comprises a load cell and electronics (601), a swelling pressure cell surrounded by heating/isolating wrap (603) and a displacement wheel (605) to initially position the swelling gap. The device may also be mounted in a multipurpose mechanical testing device. The multipurpose mechanical testing device comprises a temperature control system and a computer which will monitor the load and settings for each operation. The shaft may be wrapped in insulating fabric to minimize temperature gradients.

Experiment on Oil Swellable Material

Rubber samples were cut out of sheets with a circular diameter of about 29 mm and a sheet thickness of about 2 mm. In a non-limiting example, four disks were stacked together. The total sample thickness was 9 mm after temperature equilibrium at 82° C. (180° F.). In a series of experiments, the shaft was positioned successively to different heights giving different gaps of 0.9, 1.8, 2.7, and 3.6 mm, in order to obtain, respectively, 10, 20, 30, and 40% volumetric swelling before confinement. FIG. 1 depicts the configuration used for this experiment. In non-limiting examples, the sample is prepared to have the same diameter as the inner tube diameter to prevent swelling in a radial direction. The swelling in this case is in one direction and the state of stress may not be hydrostatic. The swelling pressure will reach zero before the swelling reached the free equilibrium value of 90-100%.

The free swelling equilibrium of the sample material was measured independently by immersing a sample in a solvent with no confinement at a desired temperature until the swollen volumes stabilizes. The sample studied in this experiment swells to about 90-100% in LVT 200 (aliphatic hydrocarbon or hydrotreated light petroleum distillates) depending on the batch and the sample geometry.

Figure 7:
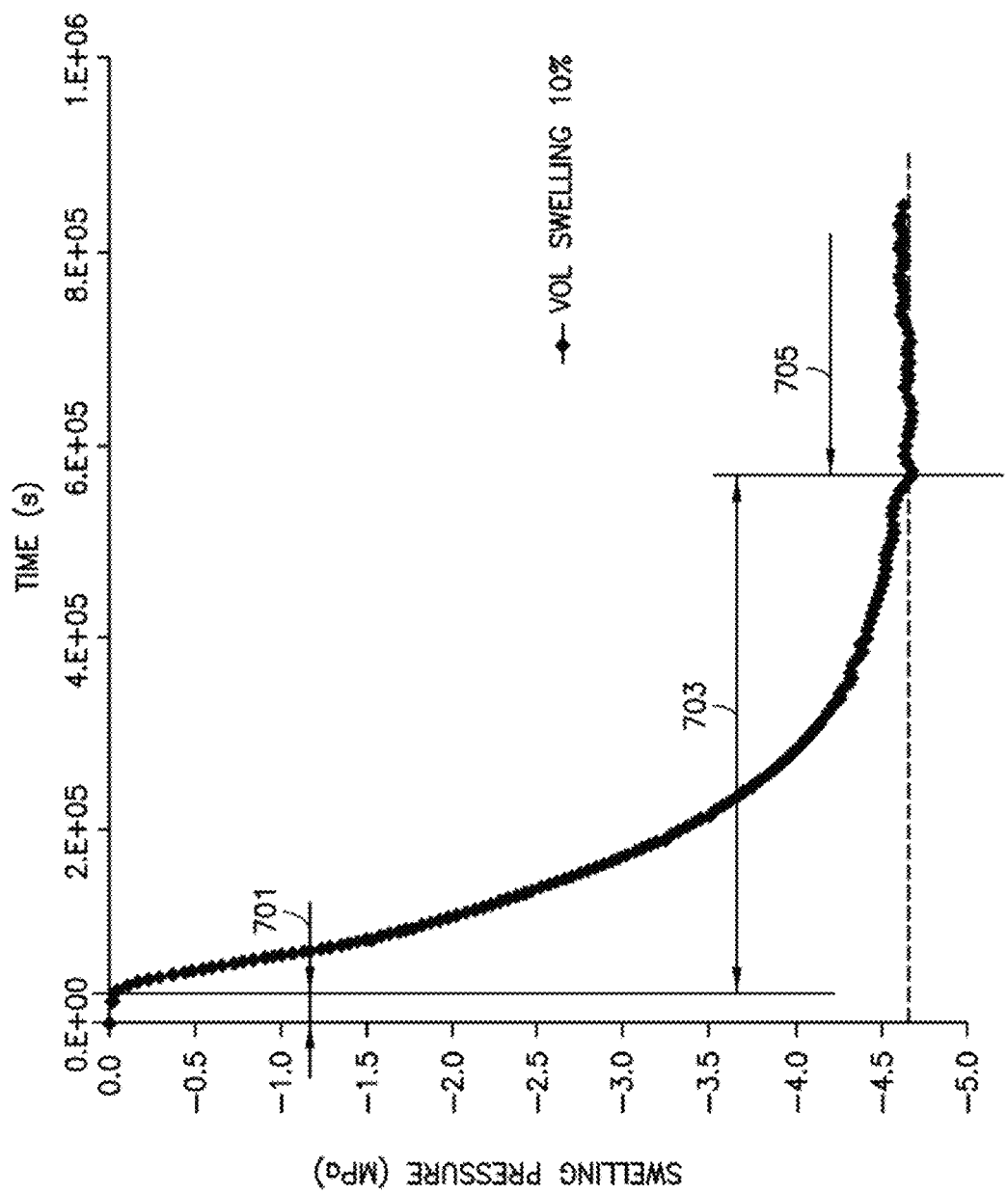
FIG. 7 depicts a graph of the experimental results for the confined swelling pressure for an oil-swellable rubber material.

FIG. 7 depicts a graph of the experimental results for the confined swelling pressure for an oil-swellable rubber material. The swelling pressure is shown over time with a gap corresponding to 10% free swelling. FIG. 7 depicts a graph of the results recorded after the oil was introduced into the confinement setup with only the initial phase of the experiment depicted in this graph. The shaft was positioned to require 10% volumetric swelling before initial contact with the piston. In a first phase (701), no load is recorded. The sample swells until it contacts the upper support. In a second phase (703), a load is recorded as the sample begins to apply a force (swelling pressure) against the axial confinement. The magnitude of the load slowly increases until it reaches equilibrium in the third phase (705). For this particular experiment, initial equilibrium as depicted in FIG. 7, required about 1 week.

At the beginning of the second phase (703), the sample is swollen in a non-homogeneous way i.e. the solvent just started diffusing in the material close to the ceramic plates. The local solvent concentration close to the ceramic plates is high and the swelling pressure is therefore low. During the second phase (703), the total volume (sample and solvent) is kept approximately constant but the solvent slowly diffuses through the sample until the solvent concentration gradient cancels out.

During the third phase, the solvent is homogeneously distributed throughout the sample and the local solvent concentration equals the global concentration. The solvent concentration is now at its lowest value and generates the highest swelling pressure.

The experiment continues with the piston being moved up to increase the gap in order to require a 20% total volume swelling. The load is then recorded until the sample re-equilibrates. The same processes are followed for a swelling increase of 30% and 40%.

Figure 8:
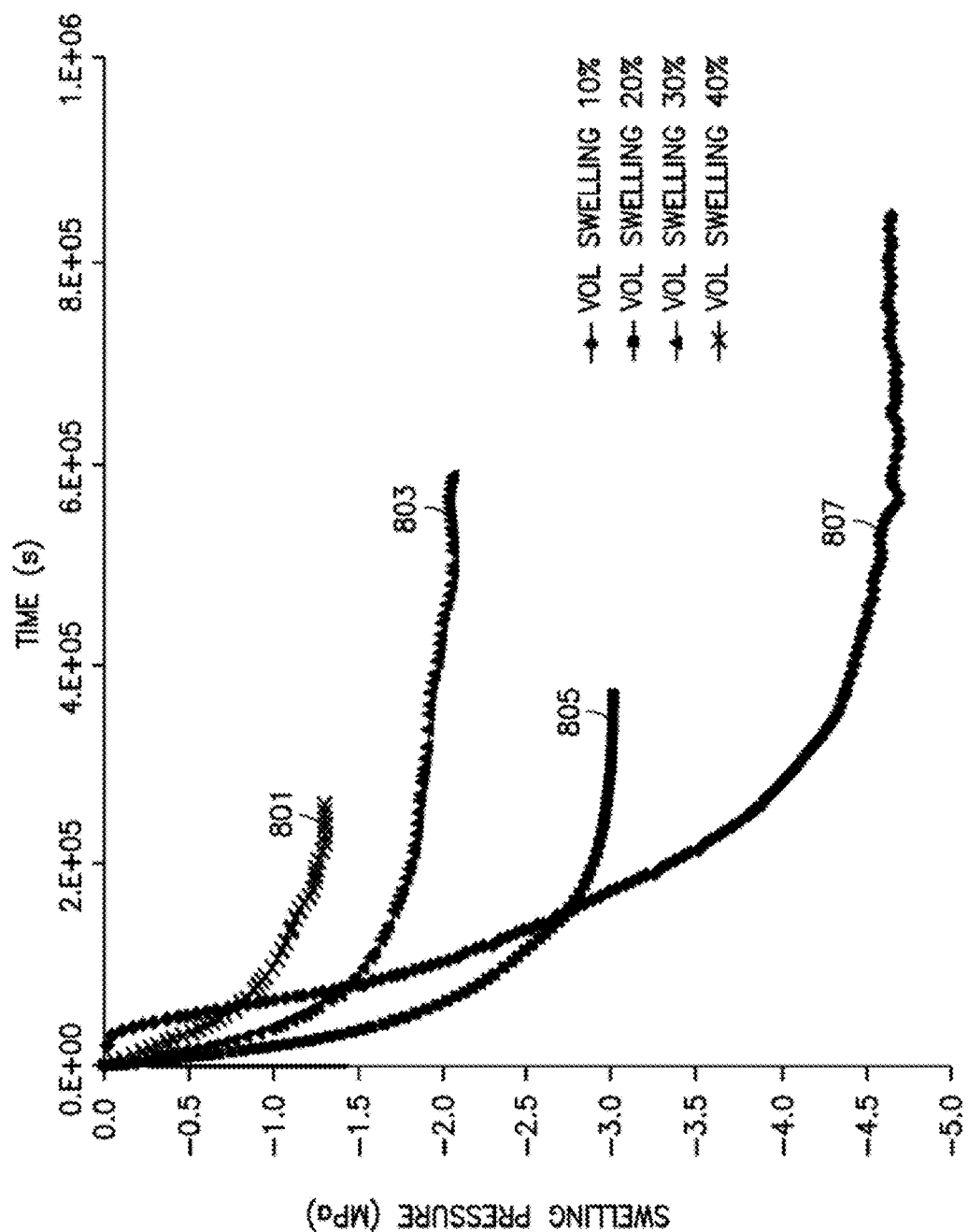
FIG. 8 depicts a graph of the confined swelling pressure for oil swellable rubber at 10, 20, 30, and 40% swelling.

FIG. 8 depicts the swelling pressure as a function of time for four experimental stages, corresponding to swelling confinements of 10, 20, 30, and 40% swelling. The experiments were conducted sequentially on the same sample. FIG. 8 shows the results for the four successive tests on the same sample, graph (807) shows a volume swelling of 10%, graph (805) shows a volume swelling of 20%, graph (603) shows a volume swelling of 30% and graph (801) shows a volume swelling of 40%. As intuitively expected and quantitatively modeled the higher the swelling ratio, the lower the swelling pressure. See Cai et al., "Force generated by a swelling elastomer subject to constraint", 107, 103535 (2010) and Lou et al., "Swellable elastomers under constraint", Journal of Applied Physics 112, 034906 (2012), the contents of both are herein incorporated by reference in their entirety.

Figure 9:
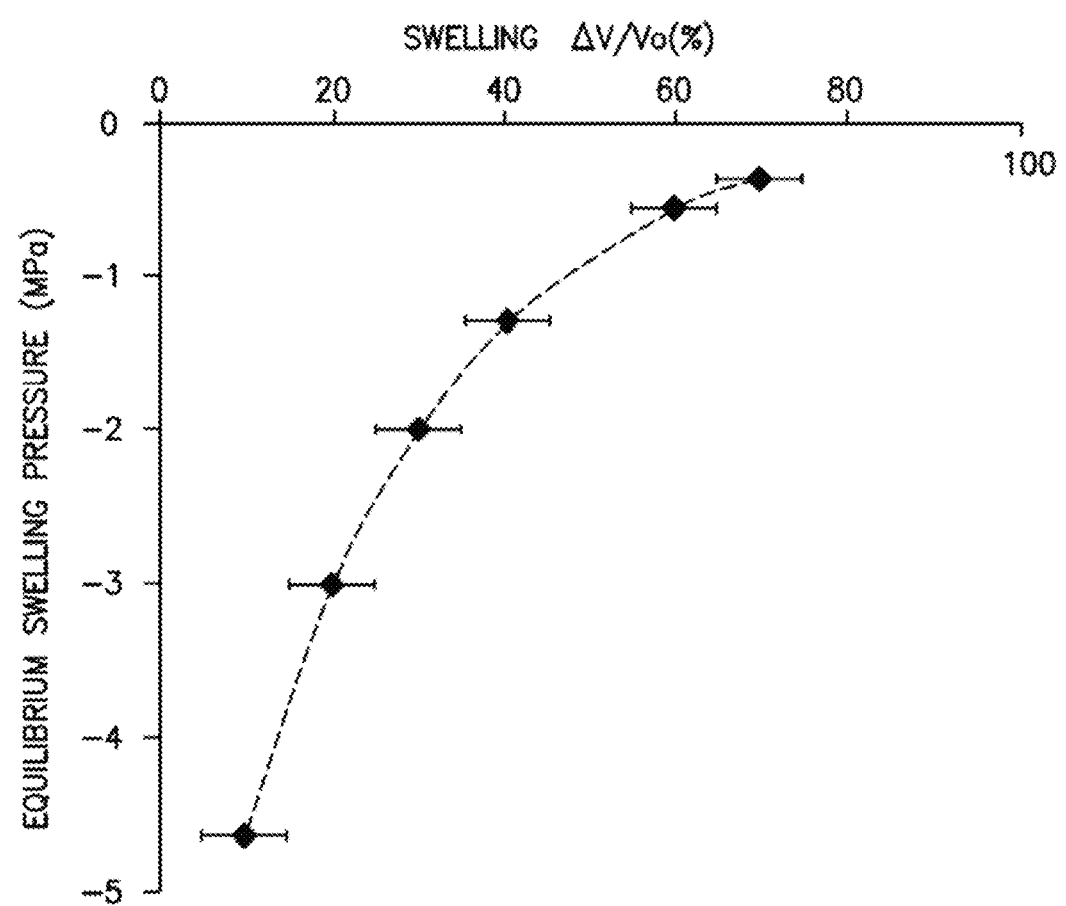
FIG. 9 depicts a graph of the swelling pressure as a function of the swelling.

FIG. 9 depicts a graph of the equilibrium swelling pressure as a function of the free swelling required before confinement which is at 10%, 20%, 30%, and 40% swelling.

The example illustrates that the apparatus and method of the subject disclosure can be used to characterize both the kinetics of swelling and the maximum swelling pressure that is generated under a variety of conditions.

Experiments on Cement Paste with an Expanding Additive (with External Water)

In an embodiment, a thin layer of high temperature lubricant was painted on the outer surface of the piston and bottom plug and the inner surface of the confinement cylinder. The lubricant prevents adhesion of the cement to the metal surfaces, reducing friction of the piston and preventing metal oxidation. After assembling the lubricated device, the device was preheated to a desired temperature, which in this case was 85° C.

A cement slurry comprising a specific recipe which included an expanding additive was prepared in the laboratory using a small blender. The fresh slurry was then poured into the confinement cylinder to a height of about 2 inches, which in this instance required about 35 g of slurry. A porous ceramic disk was saturated with water and then placed on top of the cement slurry, with a layer of filter paper between the porous ceramic disk and the cement to keep the disk clean. The disk simulates a permeable formation containing water that can flow into the cement. As the cement and expanding agent react, internal volume lost to chemical shrinkage is replaced by water flowing into the paste, keeping the pores of the sample saturated as the cement hydrates and sets.

Quickly, the piston was then inserted into the cylinder until it made contact with the porous disk. The piston has small openings that allow water to move axially through the piston head. Additional water was poured on top of the piston to provide an additional reservoir available to the sample, and then finally a layer of high-boiling-point silicon oil was added to prevent evaporation of the water. FIG. 2 above depicts this experimental configuration.

Figure 10A:
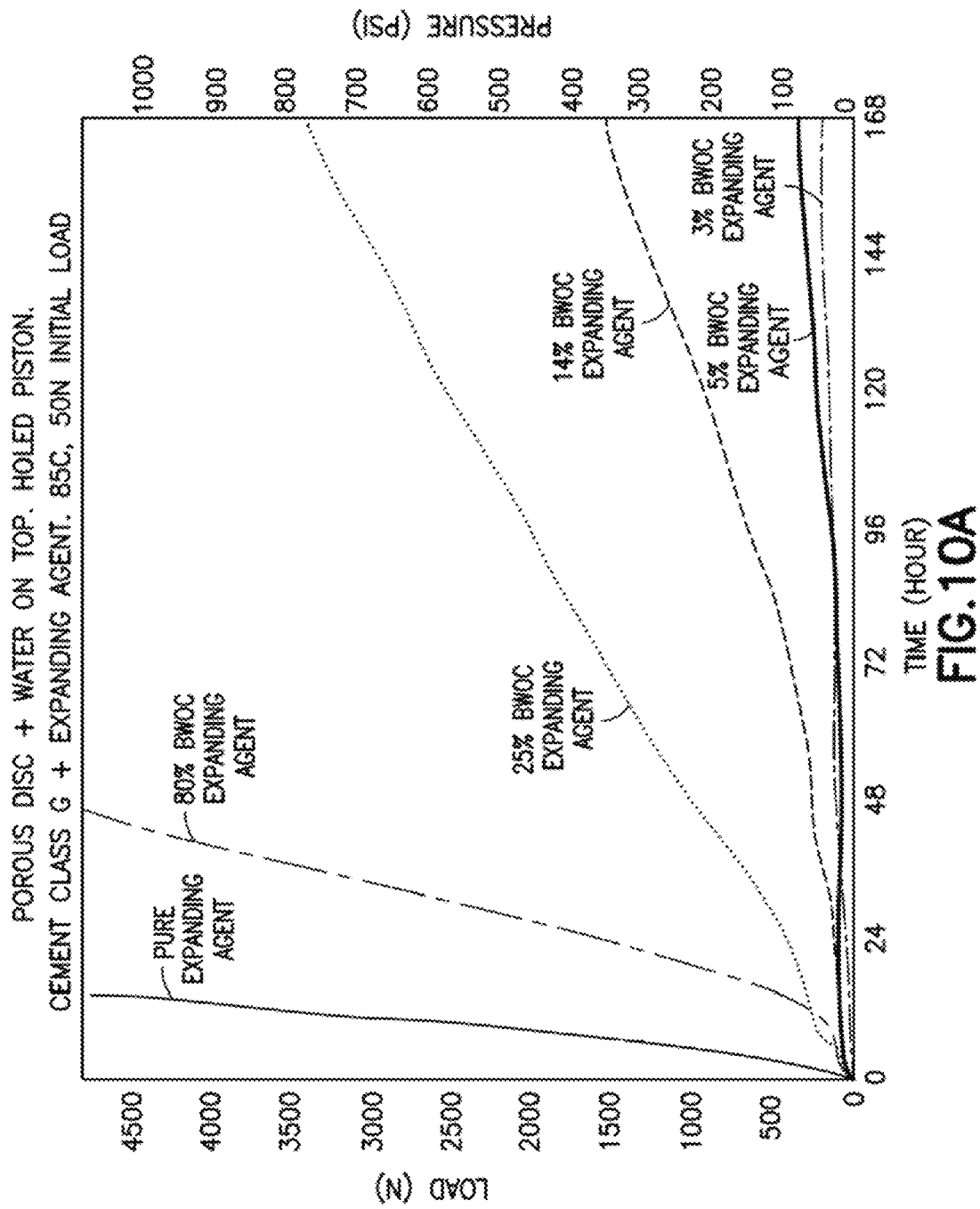

In an embodiment, the device was placed into a multi-purpose testing machine and the piston was locked to the shaft. The testing machine interfaces with a computer processor where the load and displacement are measured versus time while the data is recorded in a file. The testing machine for this experiment was programmed to apply a small initial load of 50 N and then to maintain a fixed displacement of the piston for the remainder of the experiment. As the sample tries to expand, the load increases to hold the piston in place. FIG. 10A show the results for a series of experiments conducted with different levels of expanding agents. FIG. 10A is a graph of the confinement load (left axis) and corresponding pre-stress (right axis) developed in expanding cement slurries at 85° C. with a supply of external water. Experiments on Cement Paste with an Expanding Additive (No External Water)

Additional tests were conducted under the same conditions as the experiment with external water but in this case the porous water filled disk was not used. Instead, the piston head contacted the cement slurry directly. This stimulates hydration of cement placed against a tight formation that supplies no water to the cement. In this case, internal shrinkage will desaturate the pore system, causing some shrinkage that may be counteracted by the expansion. For this configuration, a piston with no openings was used and a thick layer of lubricant grease was applied around the piston to prevent water evaporation from the sample. FIG. 10B show the results for a series of experiments conducted with different levels of expanding agents. FIG. 10B is a graph of the confinement load (left axis) and corresponding pre-stress (right axis) developed in expanding cement slurries at 85° C. without a supply of external water.

In a further experiment, the piston applies an initial load of 50 N; this is a small pressure to ensure the piston is in contact with the sample. The piston is locked into position and for 4-5 days the piston will keep the displacement by increasing the load. The cement has plenty of time to set and displays significant mechanical properties. The load is then reduced to about 100 N. A load/strain curve is then used to calculate the energy stored in the cement. The load of about 100 N will be kept constant for about 24 hours while the instrument will measure the strain (if the cement is still able to expand).

These tests help us to simulate how the cement sheath behaves (once it has hardened downhole) and alter a pressure drop (due for instance to casing or formation movement). These tests are particularly important to verify if the cement is still able to follow the casing/formation movement, thus preventing the formation of micro-annuli.

In view of the above description it will be appreciated that features of the subject disclosure may be implemented in computer programs stored on a computer readable medium and run by processors, application specific integrated circuits and other hardware. Moreover, the computer programs and hardware may be distributed across devices including, but not limited to equipment which is located at the surface, whether onsite or elsewhere.

Although only a few examples have been described in detail above, those skilled in the art will readily appreciate that many modifications are possible in the examples without materially departing from this subject disclosure. Accordingly, all such modifications are intended to be included within the scope of this disclosure as defined in the following claims. In the claims, means-plus-function clauses are intended to cover the structures described herein as performing the recited function and not only structural equivalents, but also equivalent structures. Thus, although a nail and a screw may not be structural equivalents in that a nail employs a cylindrical surface to secure wooden parts together, whereas a screw employs a helical surface, in the environment of fastening wooden parts, a nail and a screw may be equivalent structures. It is the express intention of the applicant not to invoke 35 U.S.C. §112, paragraph 6 for any limitations of any of the claims herein, except for those in which the claim expressly uses the Words 'means for' together with an associated function.

What is claimed is:

1. A confinement device for measuring a swelling pressure and swelling kinetics of a sample comprising:
   an external fluid filled container;
   an internal container disposed inside the external container wherein the internal container has openings that allow fluid flow from the external fluid filled container into the internal container;
   a base member coupling the external and internal container, the base member comprising a heating element;
   a sample inside the internal container wherein the sample swells on contact with the fluid;
   a piston operative to slide axially inside the internal container; and
   a mechanical testing device connected to the piston to determine at least one of a force and a displacement exerted by the sample on the piston as the sample swells, wherein the internal container confines the sample in a radial direction and the piston confines the sample in an axial direction.

2. The confinement device of claim 1, where the openings enable fluid flow above and below the sample.

3. The confinement device of claim 1, wherein the piston is located on top of the sample.

4. The confinement device of claim 1, wherein the mechanical testing device comprises a load cell configured to measure the force.

5. The confinement device of claim 1, wherein the mechanical testing device comprises a sensor module configured to measure piston displacement.

6. The confinement device of claim 1, wherein the fluid is at least one of oil and water.

7. The confinement device of claim 1, wherein the heating element is used to keep the sample at a fixed temperature.

8. The confinement device of claim 1, wherein the sample is a solid sample or a liquid sample.

9. The confinement device of claim 1, wherein the internal and external containers are at a temperature below a boiling point of the sample.

10. The confinement device of claim 1, wherein the apparatus is placed inside a high pressure chamber.

11. The confinement device of claim 1, wherein a piston head of the piston has a plurality of openings to allow fluid to axially move through the piston head.

12. The confinement device of claim 1, wherein the piston is locked in a fixed position inside the internal container.

13. The confinement device of claim 1, wherein the fluid is at least one of oil and water.

14. The confinement device of claim 1, further comprising a lower support member located below the sample, a bottom portion of the lower support member comprising a slot.

15. The confinement device of claim 14, wherein the lower support member comprises at least one o-ring which seals the internal container.

16. The confinement device of claim 1, further comprising at least one fluid filled porous ceramic disk positioned on top of or on a bottom of the sample wherein the fluid from the porous ceramic disk diffuses in an axial direction into the sample.

17. The confinement device of claim 16, further comprising a gap between the sample and the at least one fluid filled porous ceramic disk.

18. The confinement device of claim 1, further comprising a gap between the sample and the piston.

19. The confinement device of claim 18, wherein the sample is able to swell before axial confinement by the piston as a result of the gap.

20. The confinement device of claim 1, wherein the internal container has a thin wall deformable portion adjacent to the sample.

21. The confinement device of claim 20, further comprising a strain gauge fitted to the external surface of the thin wall deformable portion of the internal container wherein the strain gauge measures a radial strain of the sample acting on the internal container wall.

22. A method for evaluating a sample of material used for zonal isolation, the method comprising:
    using a confinement device comprising an external fluid filled container and an internal container disposed inside the external container wherein the internal container has openings that allow fluid flow from the external fluid filled container into the internal container;
    placing a sample of material inside the internal container, wherein the material swells on contact with a fluid;
    coupling the external and internal container with a base member comprising a heating module;
    placing a piston above the sample of material, the piston operative to slide axially inside the internal container; and
    using a mechanical testing device in contact with the piston and determining at least one of a force and a displacement exerted by the sample of material on the piston as the sample of material swells.

23. The method of claim 22, further comprising wherein the mechanical testing device comprises a load cell.

24. The method of claim 23, further comprising determining a force exerted by the sample of material on the piston using the load cell configured to measure the force over time.

* * * * *